(12) United States Patent
Zhang et al.

(10) Patent No.: US 11,282,183 B1
(45) Date of Patent: Mar. 22, 2022

(54) ROCK BRITTLENESS ANALYSIS METHOD AND SYSTEM BASED ON MINERAL CONTENT AND DISTRIBUTION AND DEVICE

(71) Applicant: INSTITUTE OF GEOLOGY AND GEOPHYSICS, CHINESE ACADEMY OF SCIENCES, Beijing (CN)

(72) Inventors: Wang Zhang, Beijing (CN); Boye Fu, Beijing (CN); Guanfang Li, Beijing (CN); Wenyang Wang, Beijing (CN); Xiaocai Shan, Beijing (CN); Fei Tian, Beijing (CN)

(73) Assignee: INSTITUTE OF GEOLOGY AND GEOPHYSICS, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 17/471,195

(22) Filed: Sep. 10, 2021

(30) Foreign Application Priority Data

Apr. 29, 2021 (CN) .......................... 202110469932.0

(51) Int. Cl.
| | |
|---|---|
| *G01N 29/07* | (2006.01) |
| *G01N 33/24* | (2006.01) |
| *G06T 7/00* | (2017.01) |

(52) U.S. Cl.
CPC ............ *G06T 7/0002* (2013.01); *G01N 29/07* (2013.01); *G01N 33/24* (2013.01);
(Continued)

(58) Field of Classification Search
CPC ......... G06T 7/0002; G06T 2207/20021; G06T 2207/30181; G01N 29/07; G01N 33/24;
(Continued)

(56) References Cited

U.S. PATENT DOCUMENTS

| | | | |
|---|---|---|---|
| 2011/0218737 A1 | 9/2011 | Gulati | |
| 2013/0259190 A1* | 10/2013 | Walls | G01N 33/24 |
| | | | 378/9 |

(Continued)

FOREIGN PATENT DOCUMENTS

| | | | | |
|---|---|---|---|---|
| CN | 104502971 A | | 4/2015 | |
| CN | 105445440 | * | 3/2016 | ............ G01N 33/24 |

(Continued)

OTHER PUBLICATIONS

Xiaoyan Qin, et al., A new shale brittleness evaluation method based on rock physics and mineral compositions, Natural Gas Geoscience, 2016, pp. 1924-1941, vol. 27 No. 10.
(Continued)

*Primary Examiner* — Jacques M Saint Surin
(74) *Attorney, Agent, or Firm* — Bayramoglu Law Offices LLC

(57) ABSTRACT

A rock brittleness analysis method and system based on mineral content and distribution, and a device are provided. The rock brittleness analysis method includes: performing digital processing on an image of a rock, and performing an autocorrelation analysis on a two-dimensional (2D) array obtained after the digital processing to obtain an autocorrelation coefficient variation curve; using an abscissa value corresponding to an ordinate value of dropping to 1/e on the autocorrelation coefficient variation curve to be an autocorrelation length of the rock; constructing an autocorrelation function for describing a mineral distribution according to the autocorrelation length and the distribution characteristics of a mineral and an elastic modulus in the rock; reconstructing a rock sample of the rock to obtain density and elastic modulus distributions of the rock; and partitioning meshes of the reconstructed rock sample to obtain a brittleness index distribution of the to-be-analyzed rock partitioned in different scales.

16 Claims, 4 Drawing Sheets

(52) U.S. Cl.
CPC .. *G01N 2291/011* (2013.01); *G01N 2291/023* (2013.01); *G01N 2291/02827* (2013.01); *G01N 2291/0421* (2013.01); *G06T 2207/20021* (2013.01); *G06T 2207/30181* (2013.01)

(58) Field of Classification Search
CPC ....... G01N 2291/023; G01N 2291/011; G01N 2291/02827; G01N 2291/0421
USPC ......................................................... 382/109
See application file for complete search history.

(56) References Cited

U.S. PATENT DOCUMENTS

| | | | | |
|---|---|---|---|---|
| 2013/0308631 | A1* | 11/2013 | Dingler | H04L 12/14 370/352 |
| 2014/0044315 | A1* | 2/2014 | Derzhi | G06T 7/0004 382/109 |
| 2018/0238774 | A1* | 8/2018 | Amendt | G01N 3/08 |

FOREIGN PATENT DOCUMENTS

| | | | | |
|---|---|---|---|---|
| CN | 107290219 | A | 10/2017 | |
| CN | 109490965 | A | 3/2019 | |
| CN | 109782348 | A | 5/2019 | |
| CN | 109828031 | * | 5/2019 | ............... G01N 3/08 |
| CN | 110851937 | A | 2/2020 | |
| CN | 111398273 | * | 7/2020 | ............... G01N 3/08 |
| CN | 112986247 | * | 6/2021 | ............... G01N 21/84 |
| WO | WO 2011112294 | * | 9/2011 | ............... G06F 7/60 |
| WO | 2018175404 | A1 | 9/2018 | |
| WO | 2019117857 | A1 | 6/2019 | |

OTHER PUBLICATIONS

Wen Tao, et al., Evaluation of methods for determining rock brittleness under compression, Journal of Natural Gas Science and Engineering, 2020, 103321, 78.

* cited by examiner

ROCK BRITTLENESS ANALYSIS METHOD AND SYSTEM BASED ON MINERAL CONTENT AND DISTRIBUTION AND DEVICE

CROSS REFERENCE TO THE RELATED APPLICATIONS

This application is based upon and claims priority to Chinese Patent Application No. 202110469932.0, filed on Apr. 29, 2021, the entire contents of which are incorporated herein by reference.

TECHNICAL FIELD

The present invention belongs to the field of medium brittleness distribution characterization, and more particularly relates to a rock brittleness analysis method and system based on mineral content and distribution, and a device.

BACKGROUND

With the further research of oil and gas development technology and the increasing demand for unconventional oil and gas resources, the demand for underground medium fracturing is increasing. Since the selection of the perforation position in the process of rock fracturing is closely related to the brittleness of the rock, it is necessary to study the brittleness evaluation standard of the rock in depth to provide a basis for the selection of the rock fracturing location. The brittleness characteristics of the rock is greatly affected by the types and distribution of minerals in the rock. Therefore, when studying the brittleness characteristics of the real rock, it is required to fully calculate the influences of the types and distribution of minerals on the elastic properties of the rock. The conventional rock brittleness analysis method, however, only calculates the influence of the types of minerals in the rock on the brittleness characteristics of the rock. It lacks in-depth study in the difference in rock brittleness distribution caused by the difference in mineral distribution of the rock and the influence of the difference on the brittleness characteristics of the rock. The mineral distribution determines the structural characteristics of the rock and is an important factor affecting the elastic properties of the rock.

The autocorrelation function is an effective method to describe the random distribution of substances. Through the control of its power spectrum function, the different mineral distribution of the rock can be characterized, so as to quantitatively calculate the influence of the mineral distribution on various characteristics of the rock. The digital core technology can be used to display the internal structure of the rock based on two-dimensional (2D) scanning electron microscope (SEM) imaging or three-dimensional (3D) computed tomography (CT) scanning in combination with the image processing technology. The digital core technology can be used to study the internal mineral distribution of the rock. In addition, the digital core technology can be combined with a rock brittleness index characterization algorithm to reflect the influence of the internal mineral distribution of the rock on the spatial distribution of rock brittleness. Under the non-uniform mineral distribution of the rock, studying an autocorrelation function for describing the mineral distribution characteristics and calculating the distribution characteristics of the brittleness index is an important method for studying the brittleness distribution of the rock and an important basis for selecting the rock fracturing location.

However, the correlation analysis of rock brittleness characteristics in the prior art only considers the influence of the mineral content and ignores the influence of the mineral distribution, and it lacks an effective method for quantitative description of the mineral distribution. Therefore, the analysis of rock brittleness based on the quantitative characterization of mineral distribution is still a topic that needs to be studied in the art.

SUMMARY

The present invention provides a rock brittleness analysis method based on mineral content and distribution. The present invention aims to solve the problem that the existing rock brittleness analysis method in the prior art only considers the internal mineral content and ignores the mineral distribution, which causes the accuracy and precision of the analysis result to fail to meet expectations. The method includes:

step S10: performing digital processing on an image of a to-be-analyzed rock, and performing an autocorrelation analysis on a two-dimensional (2D) array obtained after the digital processing to obtain an autocorrelation coefficient variation curve;

step S20: using an abscissa value corresponding to an ordinate value of dropping to 1/e on the autocorrelation coefficient variation curve to be an autocorrelation length of the to-be-analyzed rock;

step S30: constructing an autocorrelation function for describing a mineral distribution according to the autocorrelation length of the to-be-analyzed rock and distribution characteristics of a mineral and an elastic modulus in the to-be-analyzed rock;

step S40: reconstructing a rock sample of the to-be-analyzed rock according to the autocorrelation function to obtain density and elastic modulus distributions of the to-be-analyzed rock; and step S50: partitioning meshes of the reconstructed rock sample according to the density and elastic modulus distributions of the to-be-analyzed rock to obtain a brittleness index distribution of the to-be-analyzed rock partitioned in different scales.

In some preferred embodiments, the autocorrelation function for describing the mineral distribution may be expressed as:

$$\Phi(x, z) = \exp\left[-\frac{r}{a}\right],$$

where, a is the autocorrelation length of the to-be-analyzed rock; $r=\sqrt{x^2+z^2}$ is a relative distance between a data point (x,z) and a rock core slice center (0,0); x and z are an abscissa value and an ordinate value of the data point (x,z), respectively.

In some preferred embodiments, the density and elastic modulus distributions of the to-be-analyzed rock may be expressed as follows:

$$\begin{cases} \rho(x, z) = \rho_0[1 + \varepsilon_\rho(x, z)]; & \langle \varepsilon_\rho \rangle = 0 \\ K(x, z) = K_0[1 + \varepsilon_K(x, z)]; & \langle \varepsilon_K \rangle = 0, \\ \mu(x, z) = \mu_0[1 + \varepsilon_\mu(x, z)]; & \langle \varepsilon_\mu \rangle = 0 \end{cases}$$

where, $\rho(x,z)$ is a density at the data point (x,z), and $\rho_0$ is a background density of the to-be-analyzed rock; $K(x,z)$ is a bulk modulus at the data point (x,z), and $K_0$ is a background value of the bulk modulus; $\mu(x,z)$ is a shear modulus at the data point (x,z), and $\mu_0$ is a background value of the shear modulus; x and z are the abscissa value and the ordinate value of the data point (x,z), respectively; ε is a perturbation quantity, $\varepsilon_\rho$ is a density perturbation generated by rock heterogeneity; $\varepsilon_K$ is a bulk modulus perturbation generated by the rock heterogeneity; $\varepsilon_\mu$ is a shear modulus perturbation generated by the rock heterogeneity; $\langle \ \rangle$ represents an averaging operation.

In some preferred embodiments, the background value $\mu_0$ of the shear modulus and the background value $K_0$ of the bulk modulus may be respectively calculated by a pore acoustic elasticity equation:

$$K_0 = \frac{4}{3}\rho_0 V_P^2 - \rho_0 V_S^2,$$

$$\mu_0 = \rho_0 V_S^2,$$

where, $V_P$ and $V_S$ are respectively a longitudinal wave velocity and a transverse wave velocity of the to-be-analyzed rock, and are measured by a petrophysical experiment.

In some preferred embodiments, the perturbation quantity ε may be determined by a variance and a covariance of the perturbation, and a relationship between the variance and the covariance of the perturbation may be:

$$\Phi(x,z)=C(x,z)/\sigma^2,$$

where, $C(x,z)$ is the covariance of the perturbation, $\sigma^2$ is the variance of the perturbation, and $\Phi(x,z)$ is the autocorrelation function for describing the mineral distribution.

In some preferred embodiments, the brittleness index of each mesh partitioned in step S50 may be calculated as follows:

$$E_{BI} = \frac{E - E_{min}}{E_{max} - E_{min}},$$

$$\upsilon_{BI} = \frac{\upsilon - \upsilon_{max}}{\upsilon_{max} - \upsilon_{min}},$$

$$B1 = \frac{E_{BI} + \upsilon_{BI}}{2},$$

where, $E_{max}$, $E_{min}$, E and $E_{BI}$ respectively represent a maximum Young's modulus, a minimum Young's modulus and an average Young's modulus in four nodes of each mesh, and a relative difference of Young's moduli of the mesh; $\upsilon_{max}$, $\upsilon_{min}$, $\upsilon$ and $\upsilon_{BI}$ respectively represent a maximum Poisson's ratio, a minimum Poisson's ratio and an average Poisson's ratio in the four nodes of each mesh, and a relative difference of Poisson's ratios of the mesh; B1 represents the brittleness index of each mesh.

In some preferred embodiments, the average Young's modulus E and the average Poisson's ratio υ of each mesh partitioned in step S50 may be calculated as follows:

$$E = \frac{E_1 + E_2 + E_3 + E_4}{4},$$

$$v = \frac{v_1 + v_2 + v_3 + v_4}{4},$$

where, $E_1$, $E_2$, $E_3$ and $E_4$ are Young's moduli of the four nodes $a_1$, $a_2$, $a_3$ and $a_4$ of the mesh, respectively; $v_1$, $v_2$, $v_3$ and $v_4$ are Poisson's ratios of the four nodes $a_1$, $a_2$, $a_3$ and $a_4$ of the mesh, respectively.

Another aspect of the present invention provides a rock brittleness analysis system based on mineral content and distribution. The system includes the following modules:

a digital processing module, configured to perform digital processing on an image of a to-be-analyzed rock to obtain a 2D array of the to-be-analyzed rock;

an autocorrelation analysis module, configured to perform an autocorrelation analysis on the 2D array, and use an abscissa value corresponding to an ordinate value of dropping to 1/e on an autocorrelation coefficient variation curve obtained after analysis to be an autocorrelation length of the to-be-analyzed rock;

an autocorrelation function construction module, configured to construct an autocorrelation function for describing a mineral distribution according to the autocorrelation length of the to-be-analyzed rock and distribution characteristics of a mineral and an elastic modulus in the to-be-analyzed rock;

a density and elastic modulus distribution calculation module, configured to reconstruct a rock sample of the to-be-analyzed rock according to the autocorrelation function to obtain density and elastic modulus distributions of the to-be-analyzed rock; and a brittleness analysis module, configured to partition meshes of the reconstructed rock sample according to the density and elastic modulus distributions of the to-be-analyzed rock to obtain a brittleness index distribution of the to-be-analyzed rock partitioned in different scales.

A third aspect of the present invention proposes an electronic device. The electronic device includes:

at least one processor; and a memory in communication connection with the at least one processor, where an instruction executable by the processor is stored on the memory, and the instruction is configured to be executed by the processor to implement the aforementioned rock brittleness analysis method based on mineral content and distribution.

A fourth aspect of the present invention proposes a computer-readable storage medium. a computer instruction is stored on the computer-readable storage medium, and the computer instruction is configured to be executed by a computer to implement the aforementioned rock brittleness analysis method based on mineral content and distribution.

The present invention has the following beneficial effects:

(1) The rock brittleness analysis method of the present invention can study the influence of the mineral distribution in the rock on the rock brittleness index by extracting the mineral distribution in the rock, thereby improving the accuracy and precision of the subsequent rock brittleness analysis.

(2) The rock brittleness analysis method of the present invention extracts the rock mineral distribution through digital core technology, obtains the internal elastic modulus perturbation distribution of the rock, and superimposes it in the equivalent elastic modulus variation caused by the acoustic elastic effect in the form of perturbation. In this way, this method establishes a more realistic numerical model of deep reservoirs, thereby further improving the accuracy and precision of subsequent rock brittleness analysis.

(3) The rock brittleness analysis method of the present invention can obtain more accurate and high-precision spatial information on the distribution of the rock brittleness index, so as to provide more accurate information for the site selection of rock fracturing.

BRIEF DESCRIPTION OF THE DRAWINGS

Other features, objectives and advantages of the present invention will become more apparent upon reading the detailed description of the non-restrictive embodiments with reference to the following drawings.

DETAILED DESCRIPTION OF THE EMBODIMENTS

Figure 1:
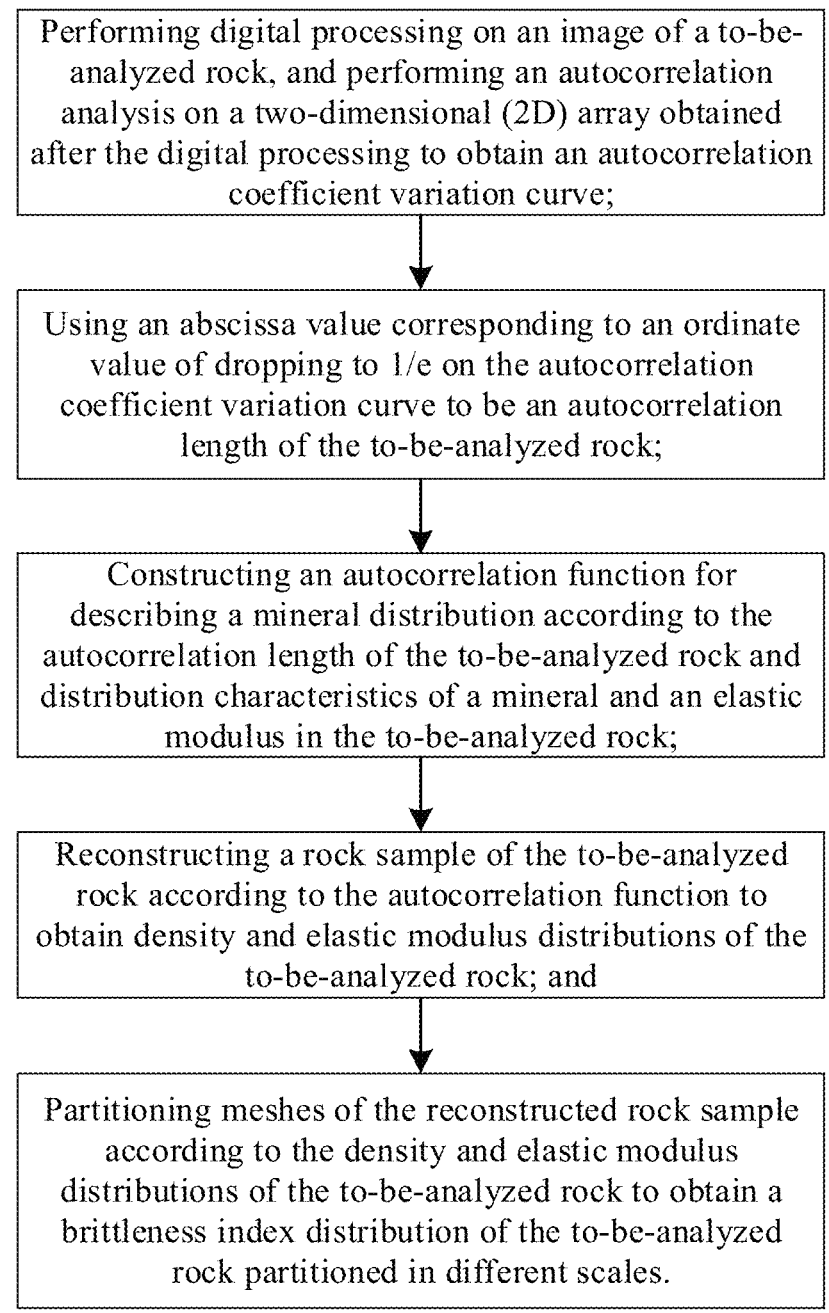
FIG. 1 is a flowchart of a rock brittleness analysis method based on mineral content and distribution provided by the present invention.

The present invention will be further described in detail below in conjunction with the drawings and embodiments. It should be understood that the specific embodiments described herein are merely intended to explain the present invention, rather than to limit the present invention. It should also be noted that, for convenience of description, only the parts related to the present invention are shown in the drawings.

It should be noted that the embodiments in the present invention and features in the embodiments may be combined with each other if no conflict occurs. The present invention will be described in detail below with reference to the drawings and embodiments.

The present invention provides a rock brittleness analysis method based on mineral content and distribution. This method fully considers the influences of variations in the relative position of particles and the pore structure in the rock on the rock brittleness characteristics, and can calculate the rock brittleness index distribution and the rock brittleness heterogeneity characteristics under a given mineral distribution, which lays the foundation for the selection of rock fracturing locations.

The rock brittleness analysis method based on mineral content and distribution provided by the present invention includes:

Step S10: Perform digital processing on an image of a to-be-analyzed rock, and perform an autocorrelation analysis on a two-dimensional (2D) array obtained after the digital processing to obtain an autocorrelation coefficient variation curve.

Step S20: Use an abscissa value corresponding to an ordinate value of dropping to 1/e on the autocorrelation coefficient variation curve to be an autocorrelation length of the to-be-analyzed rock.

Step S30: Construct an autocorrelation function for describing a mineral distribution according to the autocorrelation length of the to-be-analyzed rock and distribution characteristics of a mineral and an elastic modulus in the to-be-analyzed rock.

Step S40: Reconstruct a rock sample of the to-be-analyzed rock according to the autocorrelation function to obtain density and elastic modulus distributions of the to-be-analyzed rock.

Step S50: Partition meshes of the reconstructed rock sample according to the density and elastic modulus distributions of the to-be-analyzed rock to obtain a brittleness index distribution of the to-be-analyzed rock partitioned in different scales.

In order to more clearly describe the rock brittleness analysis method based on mineral content and distribution provided by the present invention, the steps in the embodiment of the present invention will be described in detail below in conjunction with FIG. 1.

A first embodiment of the present invention provides a rock brittleness analysis method based on mineral content and distribution. The method includes steps S10 to S50. The various steps are described in detail below.

Step S10: Perform digital processing on an image of a to-be-analyzed rock, and perform an autocorrelation analysis on a 2D array obtained after the digital processing to obtain an autocorrelation coefficient variation curve.

Figure 2:
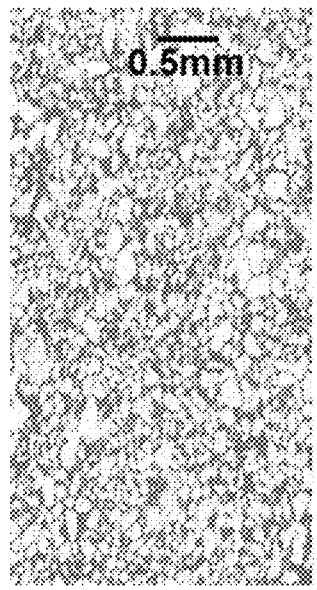
FIG. 2 shows a rock image in an embodiment of the rock brittleness analysis method based on mineral content and distribution provided by the present invention

FIG. 2 shows a rock image in an embodiment of the rock brittleness analysis method based on mineral content and distribution provided by the present invention. The digital processing of the rock image is performed to obtain a 2D array, and the autocorrelation analysis on the 2D array is performed to obtain an autocorrelation coefficient variation curve of the rock image, where 0.5 mm represents a scale of the rock image.

Step S20: Use an abscissa value corresponding to an ordinate value of dropping to 1/e on the autocorrelation coefficient variation curve to be an autocorrelation length of the to-be-analyzed rock.

The autocorrelation length of the rock is obtained according to the abscissa value and the ordinate value of the autocorrelation coefficient variation curve, and the abscissa value of the curve when the ordinate value of the curve drops to 1/e (e≈2.71828) is used as the autocorrelation length of the rock.

Figure 3:
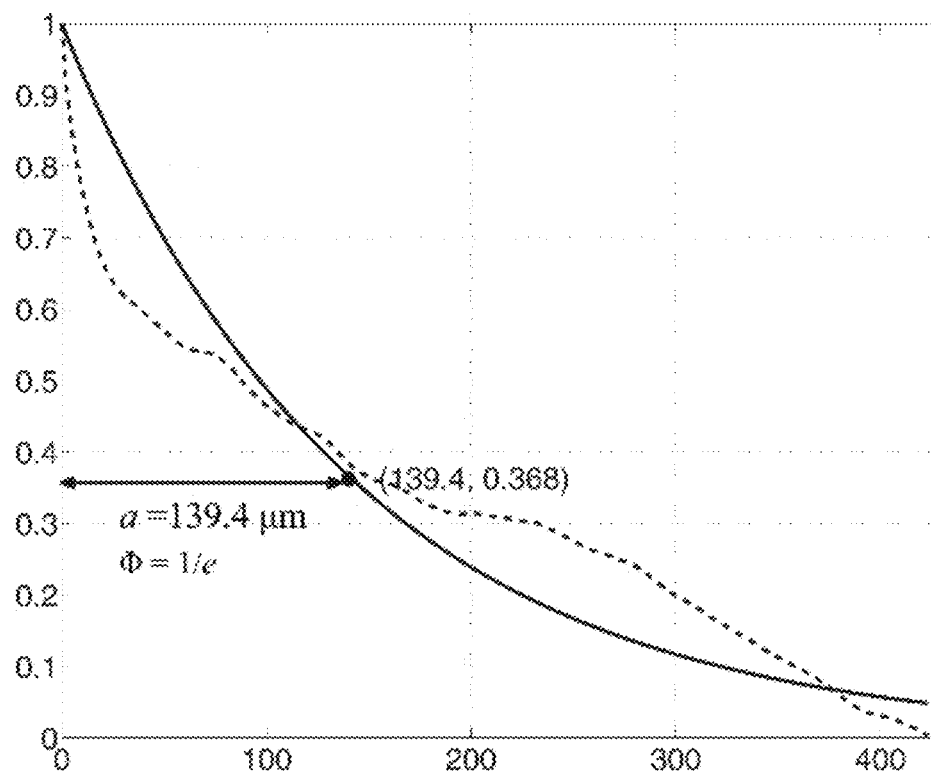
FIG. 3 shows autocorrelation coefficient variation curves extracted and theoretically calculated in an embodiment of the rock brittleness analysis method based on mineral content and distribution provided by the present invention.

FIG. 3 shows autocorrelation coefficient variation curves extracted and theoretically calculated in an embodiment of the rock brittleness analysis method based on mineral content and distribution provided by the present invention. In the figure, the dashed line represents the autocorrelation coefficient variation curve extracted from the rock image in FIG. 2, and the solid line represents the theoretical autocorrelation coefficient variation curve obtained by fitting a true autocorrelation coefficient variation curve. The units of the abscissa and the ordinate are both μm. 0.368 (1/e≈1/2.71828≈0.368) is the ordinate value when the ordinate value of the curve drops to 1/e. a=139.4 μm represents the abscissa value when the ordinate value of the autocorrelation coefficient variation curve drops to 1/e, which is used as the autocorrelation length of the rock.

Step S30: Construct an autocorrelation function for describing a mineral distribution (Eq. 1) according to the autocorrelation length of the to-be-analyzed rock and distribution characteristics of a mineral and an elastic modulus in the to-be-analyzed rock.

$$\Phi(x, z) = \exp\left[-\frac{r}{a}\right] \qquad (1)$$

where, a is the autocorrelation length of the to-be-analyzed rock; $r=\sqrt{x^2+z^2}$ is a relative distance between a data point (x,z) and a rock core slice center (0,0); x and z are an abscissa value and an ordinate value of the data point (x,z), respectively.

Step S40: Reconstruct a rock sample of the to-be-analyzed rock according to the autocorrelation function to obtain density and elastic modulus distributions of the to-be-analyzed rock.

According to the mineral distribution and the elastic modulus distribution extracted in Steps S10 and S20, spatial background values are calculated by spatial averaging. Based on the autocorrelation function obtained in Step S30, the density and elastic modulus distribution function of the to-be-analyzed rock is obtained, as shown in $$\begin{cases} \rho(x, z) = \rho_0[1 + \varepsilon_\rho(x, z)]; & \langle \varepsilon_\rho \rangle = 0 \\ K(x, z) = K_0[1 + \varepsilon_K(x, z)]; & \langle \varepsilon_K \rangle = 0 \\ \mu(x, z) = \mu_0[1 + \varepsilon_\mu(x, z)]; & \langle \varepsilon_\mu \rangle = 0 \end{cases} \quad (2)$$

where, $\rho(x,z)$ is a density at the data point (x,z), and $\rho_0$ is a background density of the to-be-analyzed rock; $K(x,z)$ is a bulk modulus at the data point (x,z), and $K_0$ is a background value of the bulk modulus; $\mu(x,z)$ is a shear modulus at the data point (x,z), and $\mu_0$ is a background value of the shear modulus; x and z are the abscissa value and the ordinate value of the data point (x,z), respectively; $\varepsilon$ is a perturbation quantity, $\varepsilon_\rho$ is a density perturbation generated by rock heterogeneity; $\varepsilon_K$ is a bulk modulus perturbation generated by the rock heterogeneity; $\varepsilon_\mu$ is a shear modulus perturbation generated by the rock heterogeneity; $\langle \ \rangle$ represents an averaging operation.

Figure 4:
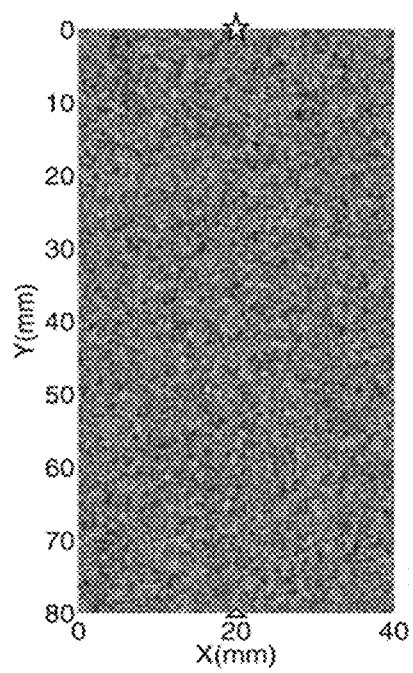
FIG. 4 shows density and elastic modulus distributions in an embodiment of the rock brittleness analysis method based on mineral content and distribution provided by the present invention.

FIG. 4 shows density and elastic modulus distributions in an embodiment of the rock brittleness analysis method based on mineral content and distribution provided by the present invention. Corresponding to the rock image in FIG. 2, the abscissa and ordinate represent the width and height of the density and elastic modulus distributions of the to-be-analyzed rock, in mm.

The background value $\mu_0$ of the shear modulus and the background value $K_0$ of the bulk modulus are respectively calculated by a pore acoustic elasticity equation, as shown in Eqs. (3) and (4):

$$K_0 = \frac{4}{3}\rho_0 V_P^2 - \rho_0 V_S^2 \quad (3)$$

$$\mu_0 = \rho_0 V_S^2 \quad (4)$$

where, $V_P$ and $V_S$ are respectively a longitudinal wave velocity and a transverse wave velocity of the to-be-analyzed rock, and are measured by a petrophysical experiment.

The perturbation quantity $\varepsilon$ is determined by a variance and a covariance of the perturbation, and a relationship between the variance and the covariance of the perturbation is expressed by Eq. (5):

$$\Phi(x,z) = C(x,z)/\sigma^2 \quad (5)$$

where, $C(x,z)$ is the covariance of the perturbation, $\sigma^2$ is the variance of the perturbation, and $\Phi(x,z)$ is the autocorrelation function for describing the mineral distribution. In an embodiment of the present invention, for moderately sorted sandstone, the variance of the perturbation is selected as 35%.

Step S50: Partition meshes of the reconstructed rock sample according to the density and elastic modulus distributions of the to-be-analyzed rock to obtain a brittleness index distribution of the to-be-analyzed rock partitioned in different scales.

The brittleness index of each mesh partitioned is calculated according to Eqs. (6) to (8):

$$E_{BI} = \frac{E - E_{min}}{E_{max} - E_{min}} \quad (6)$$

$$\upsilon_{BI} = \frac{\upsilon - \upsilon_{max}}{\upsilon_{max} - \upsilon_{min}} \quad (7)$$

$$B1 = \frac{E_{BI} + \upsilon_{BI}}{2} \quad (8)$$

where, $E_{max}$, $E_{min}$, E and $E_{BI}$ respectively represent a maximum Young's modulus, a minimum Young's modulus and an average Young's modulus in four nodes of each mesh, and a relative difference of Young's moduli of the mesh; $\upsilon_{max}$, $\upsilon_{min}$, $\upsilon$ and $\upsilon_{BI}$ respectively represent a maximum Poisson's ratio, a minimum Poisson's ratio and an average Poisson's ratio in the four nodes of each mesh, and a relative difference of Poisson's ratios of the mesh; B1 represents the brittleness index of each mesh.

The average Young's modulus E and the average Poisson's ratio $\upsilon$ of each mesh are calculated according to Eqs. (9) and (10):

$$E = \frac{E_1 + E_2 + E_3 + E_4}{4} \quad (9)$$

$$v = \frac{v_1 + v_2 + v_3 + v_4}{4} \quad (10)$$

where, $E_1$, $E_2$, $E_3$ and $E_4$ are Young's moduli of the four nodes $a_1$, $a_2$, $a_3$ and $a_4$ of the mesh, respectively; $v_1$, $v_2$, $v_3$ and $v_4$ are Poisson's ratios of the four nodes $a_1$, $a_2$, $a_3$ and $a_4$ of the mesh, respectively.

Figure 5:
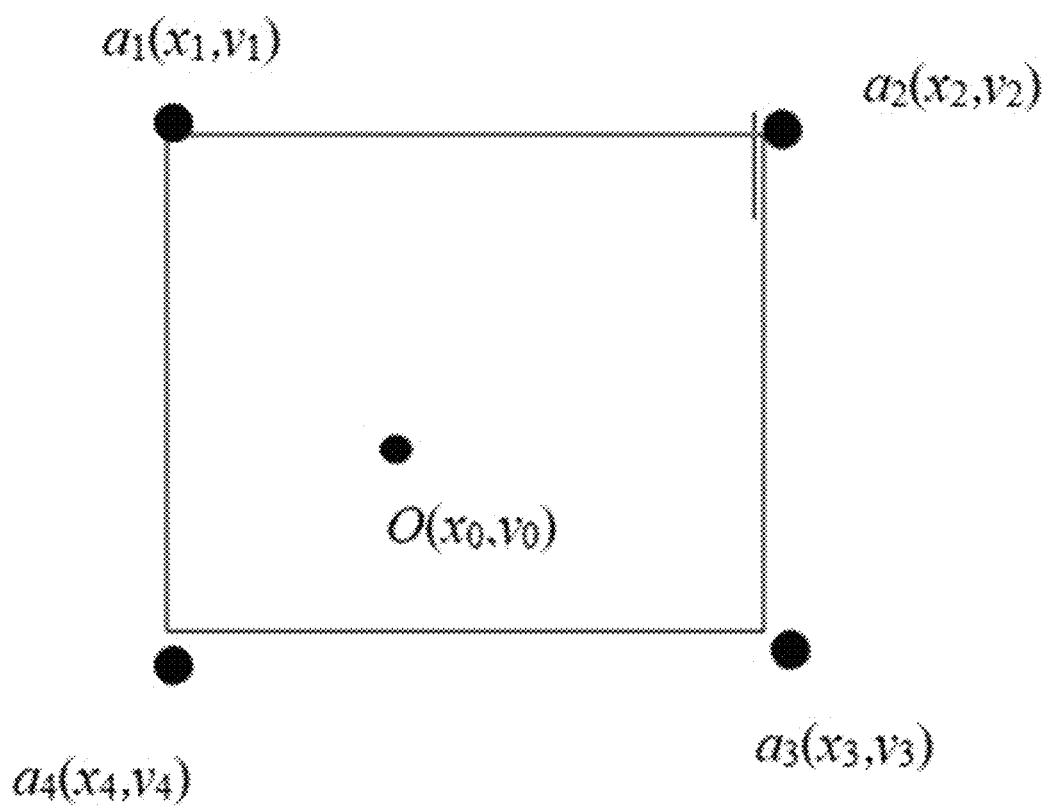
FIG. 5 shows a scale of each mesh during mesh partitioning in an embodiment of the rock brittleness analysis method based on mineral content and distribution provided by the present invention.

FIG. 5 shows a scale of each mesh during mesh partitioning in an embodiment of the rock brittleness analysis method based on mineral content and distribution provided by the present invention. In the figure, a center point O of the mesh represents a random index $C_0$ of the mesh, and a1, a2, a3 and a4 are the brittleness indexes of corner points of the mesh.

Figure 6:
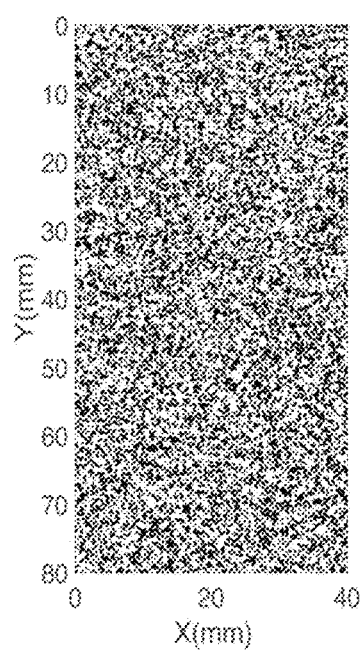
FIG. 6 shows a brittleness index distribution in an embodiment of the rock brittleness analysis method based on mineral content and distribution provided by the present invention.

FIG. 6 shows a brittleness index distribution in an embodiment of the rock brittleness analysis method based on mineral content and distribution provided by the present invention. Corresponding to the rock image in FIG. 2, the abscissa and ordinate represent the width and height of the brittleness index distribution of the to-be-analyzed rock, in mm.

These steps are described in an order in the above embodiments. However, those skilled in the art may understand that, in order to achieve the effects of these embodiments, different steps may not be necessarily executed in such an order, but may be executed simultaneously (in parallel) or in a reversed order. These simple variations should fall within the protection scope of the present invention.

A second embodiment of the present invention provides a rock brittleness analysis system based on mineral content and distribution. The system includes the following modules:

a digital processing module, configured to perform digital processing on an image of a to-be-analyzed rock to obtain a 2D array of the to-be-analyzed rock;

an autocorrelation analysis module, configured to perform an autocorrelation analysis on the 2D array, and use an abscissa value corresponding to an ordinate value of dropping to 1/e on an autocorrelation coefficient variation curve obtained after analysis to be an autocorrelation length of the to-be-analyzed rock;

an autocorrelation function construction module, configured to construct an autocorrelation function for describing a mineral distribution according to the autocorrelation length of the to-be-analyzed rock and distribution characteristics of a mineral and an elastic modulus in the to-be-analyzed rock;

a density and elastic modulus distribution calculation module, configured to reconstruct a rock sample of the to-be-analyzed rock according to the autocorrelation function to obtain density and elastic modulus distributions of the to-be-analyzed rock; and a brittleness analysis module, configured to partition meshes of the reconstructed rock sample according to the density and elastic modulus distributions of the to-be-analyzed rock to obtain a brittleness index distribution of the to-be-analyzed rock partitioned in different scales.

Those skilled in the art should clearly understand that, for convenience and brevity of description, reference is made to corresponding processes in the above method embodiments for specific working processes and related description of the system, and details are not described herein again.

It should be noted that the rock brittleness analysis system based on mineral content and distribution provided by the above embodiments is only described by taking the division of the above functional modules as an example. In practical applications, the above functions can be completed by different functional modules as required, that is, the modules or steps in the embodiments of the present invention are further decomposed or combined. For example, the modules of the above embodiments may be combined into one module, or may be further divided into multiple sub-modules to complete all or part of the functions described above. The names of the modules and steps involved in the embodiments of the present invention are only for distinguishing each module or step, and should not be regarded as improper limitations on the present invention.

A third embodiment of the present invention provides an electronic device. The electronic device includes:

at least one processor; and a memory in communication connection with the at least one processor, where an instruction executable by the processor is stored on the memory, and the instruction is configured to be executed by the processor to implement the aforementioned rock brittleness analysis method based on mineral content and distribution.

A fourth embodiment of the present invention proposes a computer-readable storage medium. a computer instruction is stored on the computer-readable storage medium, and the computer instruction is configured to be executed by a computer to implement the aforementioned rock brittleness analysis method based on mineral content and distribution.

Those skilled in the art should clearly understand that, for convenience and brevity of description, reference is made to corresponding processes in the above method embodiments for specific working processes and related description of the storage device and processing device, and details are not described herein again.

Those skilled in the art should be aware that the modules and method steps of the examples described in the embodiments disclosed herein may be implemented by electronic hardware, computer software or a combination thereof. The programs corresponding to software modules and method steps may be placed in a random access memory (RAM), an internal memory, a read-only memory (ROM), an electrically programmable ROM, an electrically erasable programmable (ROM), a register, a hard disk, a removable disk, a compact disc read-only memory (CD-ROM), or in any other form of storage medium known in the technical field. In order to clearly illustrate the interchangeability of the electronic hardware and software, the composition and steps of each example are generally described in accordance with the function in the above description. Whether the functions are performed by electronic hardware or software depends on particular applications and design constraints of the technical solutions. Those skilled in the art may use different methods to implement the described functions for each specific application, but such implementation should not be considered to be beyond the scope of the present invention.

Terms such as "first" and "second" are intended to distinguish between similar objects, rather than to necessarily describe or indicate a specific order or sequence.

In addition, terms "include", "comprise" or any other variations thereof are intended to cover non-exclusive inclusions, so that a process, a method, an article, or a device/apparatus including a series of elements not only includes those elements, but also includes other elements that are not explicitly listed, or also includes inherent elements of the process, the method, the article or the device/apparatus.

The technical solutions of the present invention are described with reference to the preferred implementations and drawings. Those skilled in the art should easily understand that the protection scope of the present invention is apparently not limited to these specific implementations. Those skilled in the art can make equivalent variations or substitutions to the relevant technical features without departing from the principles of the present invention, and the technical solutions derived by making these variations or substitutions should fall within the protection scope of the present invention.

What is claimed is:

1. A rock brittleness analysis method based on mineral content and distribution, comprising:

step S10: performing digital processing on an image of a to-be-analyzed rock, and performing an autocorrelation analysis on a two-dimensional (2D) array obtained after the digital processing to obtain an autocorrelation coefficient variation curve;

step S20: using an abscissa value corresponding to an ordinate value of dropping to 1/e on the autocorrelation coefficient variation curve to be an autocorrelation length of the to-be-analyzed rock;

step S30: constructing an autocorrelation function for describing a mineral distribution according to the autocorrelation length of the to-be-analyzed rock and distribution characteristics of a mineral and an elastic modulus in the to-be-analyzed rock:

$$\Phi(x, z) = \exp\left[-\frac{r}{a}\right],$$

wherein, a is the autocorrelation length of the to-be-analyzed rock; $r=\sqrt{x^2+z^2}$ is a relative distance between a data point (x,z) and a rock core slice center (0,0); x and z are an abscissa value and an ordinate value of the data point (x,z), respectively;

step S40: reconstructing a rock sample of the to-be-analyzed rock according to the autocorrelation function to obtain density and elastic modulus distributions of the to-be-analyzed rock:

$$\begin{cases} \rho(x,z) = \rho_0[1 + \varepsilon_\rho(x,z)]; & \langle \varepsilon_\rho \rangle = 0 \\ K(x,z) = K_0[1 + \varepsilon_K(x,z)]; & \langle \varepsilon_K \rangle = 0, \\ \mu(x,z) = \mu_0[1 + \varepsilon_\mu(x,z)]; & \langle \varepsilon_\mu \rangle = 0 \end{cases}$$

wherein, $\rho(x,z)$ is a density at the data point (x,z), and $\rho_0$ is a background density of the to-be-analyzed rock; $K(x,z)$ is a bulk modulus at the data point (x,z), and $K_0$ is a background value of the bulk modulus; $\mu(x,z)$ is a shear modulus at the data point (x,z), and $\mu_0$ is a background value of the shear modulus; x and z are the abscissa value and the ordinate value of the data point (x,z), respectively; $\varepsilon_\rho$ is a density perturbation generated by rock heterogeneity; $\varepsilon_K$ is a bulk modulus perturbation generated by the rock heterogeneity; $\varepsilon_\mu$ is a shear modulus perturbation generated by the rock heterogeneity; $\langle \ \rangle$ represents an averaging operation; and step S50: partitioning meshes of a reconstructed rock sample according to the density and elastic modulus distributions of the to-be-analyzed rock to obtain a brittleness index distribution of the to-be-analyzed rock partitioned in different scales.

2. The rock brittleness analysis method based on the mineral content and distribution according to claim 1, wherein the background value $\mu_0$ of the shear modulus and the background value $K_0$ of the bulk modulus are respectively calculated by a pore acoustic elasticity equation:

$$K_0 = \frac{4}{3}\rho_0 V_P^2 - \rho_0 V_S^2,$$
$$\mu_0 = \rho_0 V_S^2,$$

wherein, $V_P$ and $V_S$ are respectively a longitudinal wave velocity and a transverse wave velocity of the to-be-analyzed rock, and are measured by a petrophysical experiment.

3. The rock brittleness analysis method based on the mineral content and distribution according to claim 1, wherein a perturbation quantity is determined by a variance and a covariance of a perturbation; the perturbation quantity comprises the density perturbation $\varepsilon_\rho$ generated by the rock heterogeneity, the bulk modulus perturbation $\varepsilon_K$ generated by the rock heterogeneity, and the shear modulus perturbation $\varepsilon_\mu$ generated by the rock heterogeneity; a relationship between the variance and the covariance of the perturbation quantity is:

$$\Phi(x,z) = C(x,z)/\sigma^2,$$

wherein, $C(x,z)$ is the covariance of the perturbation, $\sigma^2$ is the variance of the perturbation, and $\Phi(x,z)$ is the autocorrelation function for describing the mineral distribution.

4. The rock brittleness analysis method based on the mineral content and distribution according to claim 1, wherein a brittleness index of each mesh partitioned in step S50 is calculated as follows:

$$E_{BI} = \frac{E - E_{min}}{E_{max} - E_{min}},$$
$$\upsilon_{BI} = \frac{\upsilon - \upsilon_{max}}{\upsilon_{max} - \upsilon_{min}},$$
$$BI = \frac{E_{BI} + \upsilon_{BI}}{2},$$

wherein, $E_{max}$, $E_{min}$, E and $E_{BI}$ respectively represent a maximum Young's modulus, a minimum Young's modulus and an average Young's modulus in four nodes of each mesh, and a relative difference of Young's moduli of the each mesh; $\upsilon_{max}$, $\upsilon_{min}$, $\upsilon$ and $\upsilon_{BI}$ respectively represent a maximum Poisson's ratio, a minimum Poisson's ratio and an average Poisson's ratio in the four nodes of the each mesh, and a relative difference of Poisson's ratios of the each mesh; B1 represents the brittleness index of the each mesh.

5. The rock brittleness analysis method based on the mineral content and distribution according to claim 4, wherein the average Young's modulus E and the average Poisson's ratio $\upsilon$ of the each mesh partitioned in step S50 are calculated as follows:

$$E = \frac{E_1 + E_2 + E_3 + E_4}{4},$$
$$v = \frac{v_1 + v_2 + v_3 + v_4}{4},$$

wherein, $E_1$, $E_2$, $E_3$ and $E_4$ are Young's moduli of the four nodes $a_1$, $a_2$, $a_3$ and $a_4$ of the each mesh, respectively; $v_1$, $v_2$, $v_3$ and $v_4$ are Poisson's ratios of the four nodes $a_1$, $a_2$, $a_3$ and $a_4$ of the each mesh, respectively.

6. A rock brittleness analysis system based on mineral content and distribution, comprises the following modules:

a digital processing module, configured to perform digital processing on an image of a to-be-analyzed rock to obtain a two-dimensional (2D) array of the to-be-analyzed rock;

an autocorrelation analysis module, configured to perform an autocorrelation analysis on the 2D array, and use an abscissa value corresponding to an ordinate value of dropping to 1/e on an autocorrelation coefficient variation curve obtained after the autocorrelation analysis to be an autocorrelation length of the to-be-analyzed rock;

an autocorrelation function construction module, configured to construct an autocorrelation function for describing a mineral distribution according to the autocorrelation length of the to-be-analyzed rock and distribution characteristics of a mineral and an elastic modulus in the to-be-analyzed rock:

$$\Phi(x,z) = \exp\left[-\frac{r}{a}\right],$$

wherein, a is the autocorrelation length of the to-be-analyzed rock; $r = \sqrt{x^2 + z^2}$ is a relative distance between a data point (x,z) and a rock core slice center (0,0); x and z are an abscissa value and an ordinate value of the data point (x,z), respectively;

a density and elastic modulus distribution calculation module, configured to reconstruct a rock sample of the to-be-analyzed rock according to the autocorrelation function to obtain density and elastic modulus distributions of the to-be-analyzed rock:

$$\begin{cases} \rho(x,z) = \rho_0[1+\varepsilon_\rho(x,z)]; & \langle\varepsilon_\rho\rangle = 0 \\ K(x,z) = K_0[1+\varepsilon_K(x,z)]; & \langle\varepsilon_K\rangle = 0, \\ \mu(x,z) = \mu_0[1+\varepsilon_\mu(x,z)]; & \langle\varepsilon_\mu\rangle = 0 \end{cases}$$

wherein, $\rho(x,z)$ is a density at the data point (x,z), and $\rho_0$ is a background density of the to-be-analyzed rock; $K(x,z)$ is a bulk modulus at the data point (x,z), and $K_0$ is a background value of the bulk modulus; $\mu(x,z)$ is a shear modulus at the data point (x,z), and $\mu_0$ is a background value of the shear modulus; x and z are the abscissa value and the ordinate value of the data point (x,z), respectively; $\varepsilon_\rho$ is a density perturbation generated by rock heterogeneity; $\varepsilon_K$ is a bulk modulus perturbation generated by the rock heterogeneity; $\varepsilon_\mu$ is a shear modulus perturbation generated by the rock heterogeneity; $\langle\ \rangle$ represents an averaging operation; and a brittleness analysis module, configured to partition meshes of a reconstructed rock sample according to the density and elastic modulus distributions of the to-be-analyzed rock to obtain a brittleness index distribution of the to-be-analyzed rock partitioned in different scales.

7. An electronic device, comprising:
at least one processor; and
a memory in communication connection with the at least one processor, wherein
an instruction executable by the at least one processor is stored on the memory, and the instruction is configured to be executed by the at least one processor to implement the rock brittleness analysis method based on the mineral content and distribution according to claim 1.

8. A computer-readable storage medium, wherein a computer instruction is stored on the computer-readable storage medium, and the computer instruction is configured to be executed by a computer to implement the rock brittleness analysis method based on the mineral content and distribution according to claim 1.

9. The electronic device according to claim 7, wherein the background value $\mu_0$ of the shear modulus and the background value $K_0$ of the bulk modulus are respectively calculated by a pore acoustic elasticity equation:

$$K_0 = \frac{4}{3}\rho_0 V_P^2 - \rho_0 V_S^2,$$

$$\mu_0 = \rho_0 V_S^2,$$

wherein, $V_P$ and $V_S$ are respectively a longitudinal wave velocity and a transverse wave velocity of the to-be-analyzed rock, and are measured by a petrophysical experiment.

10. The electronic device according to claim 7, wherein a perturbation quantity is determined by a variance and a covariance of a perturbation; the perturbation quantity comprises the density perturbation $\varepsilon_\rho$ generated by the rock heterogeneity, the bulk modulus perturbation $\varepsilon_K$ generated by the rock heterogeneity, and the shear modulus perturbation $\varepsilon_\mu$ generated by the rock heterogeneity; a relationship between the variance and the covariance of the perturbation quantity is:

$$\Phi(x,z) = C(x,z)/\sigma^2,$$

wherein, $C(x,z)$ is the covariance of the perturbation, $\sigma^2$ is the variance of the perturbation, and $\Phi(x,z)$ is the autocorrelation function for describing the mineral distribution.

11. The electronic device according to claim 7, wherein a brittleness index of each mesh partitioned in step S50 is calculated as follows:

$$E_{BI} = \frac{E - E_{min}}{E_{max} - E_{min}},$$

$$\upsilon_{BI} = \frac{\upsilon - \upsilon_{max}}{\upsilon_{max} - \upsilon_{min}},$$

$$BI = \frac{E_{BI} + \upsilon_{BI}}{2},$$

wherein, $E_{max}$, $E_{min}$, E and $E_{BI}$ respectively represent a maximum Young's modulus, a minimum Young's modulus and an average Young's modulus in four nodes of each mesh, and a relative difference of Young's moduli of the each mesh; $\upsilon_{max}$, $\upsilon_{min}$, $\upsilon$ and $\upsilon_{BI}$ respectively represent a maximum Poisson's ratio, a minimum Poisson's ratio and an average Poisson's ratio in the four nodes of the each mesh, and a relative difference of Poisson's ratios of the each mesh; BI represents the brittleness index of the each mesh.

12. The electronic device according to claim 11, wherein the average Young's modulus E and the average Poisson's ratio $\upsilon$ of the each mesh partitioned in step S50 are calculated as follows:

$$E = \frac{E_1 + E_2 + E_3 + E_4}{4},$$

$$v = \frac{v_1 + v_2 + v_3 + v_4}{4},$$

wherein, $E_1$, $E_2$, $E_3$ and $E_4$ are Young's moduli of the four nodes $a_1$, $a_2$, $a_3$ and $a_4$ of the each mesh, respectively; $v_1$, $v_2$, $v_3$ and $v_4$ are Poisson's ratios of the four nodes $a_1$, $a_2$, $a_3$ and $a_4$ of the each mesh, respectively.

13. The computer-readable storage medium according to claim 8, wherein the background value $\mu_0$ of the shear modulus and the background value $K_0$ of the bulk modulus are respectively calculated by a pore acoustic elasticity equation:

$$K_0 = \frac{4}{3}\rho_0 V_P^2 - \rho_0 V_S^2,$$

$$\mu_0 = \rho_0 V_S^2,$$

wherein, $V_P$ and $V_S$ are respectively a longitudinal wave velocity and a transverse wave velocity of the to-be-analyzed rock, and are measured by a petrophysical experiment.

14. The computer-readable storage medium according to claim 8, wherein a perturbation quantity is determined by a variance and a covariance of a perturbation; the perturbation quantity comprises the density perturbation $\varepsilon_\rho$ generated by the rock heterogeneity, the bulk modulus perturbation $\varepsilon_K$ generated by the rock heterogeneity, and the shear modulus perturbation $\varepsilon_\mu$ generated by the rock heterogeneity; a relationship between the variance and the covariance of the perturbation quantity is:

$$\Phi(x,z)=C(x,z)/\sigma^2,$$

wherein, $C(x,z)$ is the covariance of the perturbation, $\sigma^2$ is the variance of the perturbation, and $\Phi(x,z)$ is the autocorrelation function for describing the mineral distribution.

15. The computer-readable storage medium according to claim 8, wherein a brittleness index of each mesh partitioned in step S50 is calculated as follows:

$$E_{BI} = \frac{E - E_{min}}{E_{max} - E_{min}},$$

$$\upsilon_{BI} = \frac{\upsilon - \upsilon_{max}}{\upsilon_{max} - \upsilon_{min}},$$

$$B1 = \frac{E_{BI} + \upsilon_{BI}}{2},$$

wherein, $E_{max}$, $E_{min}$, E and $E_{BI}$ respectively represent a maximum Young's modulus, a minimum Young's modulus and an average Young's modulus in four nodes of each mesh, and a relative difference of Young's moduli of the each mesh; $\upsilon_{max}$, $\upsilon_{min}$, $\upsilon$ and $\upsilon_{BI}$ respectively represent a maximum Poisson's ratio, a minimum Poisson's ratio and an average Poisson's ratio in the four nodes of the each mesh, and a relative difference of Poisson's ratios of the each mesh; B1 represents the brittleness index of the each mesh.

16. The computer-readable storage medium according to claim 15, wherein the average Young's modulus E and the average Poisson's ratio $\upsilon$ of the each mesh partitioned in step S50 are calculated as follows:

$$E = \frac{E_1 + E_2 + E_3 + E_4}{4},$$

$$v = \frac{v_1 + v_2 + v_3 + v_4}{4},$$

wherein, $E_1$, $E_2$, $E_3$ and $E_4$ are Young's moduli of the four nodes $a_1$, $a_2$, $a_3$ and $a_4$ of the each mesh, respectively; $v_1$, $v_2$, $v_3$ and $v_4$ are Poisson's ratios of the four nodes $a_1$, $a_2$, $a_3$ and $a_4$ of the each mesh, respectively.

\* \* \* \* \*